US012758677B2

(12) United States Patent
Majhi

(10) Patent No.: US 12,758,677 B2
(45) Date of Patent: Oct. 13, 2026

(54) MATERIALS AND METHODS FOR DEODORIZATION OF MAMMALIAN URINE

(71) Applicant: Pinaki R. Majhi, Sharon, MA (US)

(72) Inventor: Pinaki R. Majhi, Sharon, MA (US)

( * ) Notice: Subject to any disclaimer, the term of this patent is extended or adjusted under 35 U.S.C. 154(b) by 0 days.

(21) Appl. No.: 18/636,138

(22) Filed: Apr. 15, 2024

(65) Prior Publication Data

US 2024/0261460 A1 Aug. 8, 2024

Related U.S. Application Data

(63) Continuation of application No. 16/754,128, filed as application No. PCT/US2018/054671 on Oct. 5, 2018, now abandoned.

(60) Provisional application No. 62/568,920, filed on Oct. 6, 2017.

(51) Int. Cl.

| | |
|---|---|
| ***A47K 11/12*** | (2006.01) |
| ***A61F 5/44*** | (2006.01) |
| ***A61F 5/441*** | (2006.01) |
| ***A61F 13/04*** | (2006.01) |
| ***A61F 13/84*** | (2006.01) |
| ***A61L 15/24*** | (2006.01) |
| ***A61L 15/46*** | (2006.01) |
| ***A61L 15/60*** | (2006.01) |

(52) U.S. Cl.

CPC .............. *A61L 15/46* (2013.01); *A47K 11/12* (2013.01); *A61F 5/4401* (2013.01); *A61F 5/441* (2013.01); *A61F 13/8405* (2013.01); *A61L 15/24* (2013.01); *A61L 15/60* (2013.01); *A61F 2013/8408* (2013.01)

(58) Field of Classification Search

CPC .... A61F 13/8405; A61F 5/441; A61F 5/4401; C08L 33/08; A61L 15/60

See application file for complete search history.

(56) References Cited

U.S. PATENT DOCUMENTS

| | | | | |
|---|---|---|---|---|
| 4,285,343 | A | | 8/1981 | McNair |
| 4,500,316 | A | | 2/1985 | Damico |
| 4,608,047 | A | | 8/1986 | Mattingly |
| 4,687,478 | A | | 8/1987 | Van Tillburg |
| 4,886,512 | A | | 12/1989 | Damico et al. |
| 4,950,264 | A | | 8/1990 | Osborn, III |
| 5,009,653 | A | | 4/1991 | Osborn, III |
| 5,085,654 | A | | 2/1992 | Buell |
| 5,129,988 | A | | 7/1992 | Farrington, Jr. |
| 5,190,563 | A | | 3/1993 | Herron et al. |
| 5,197,959 | A | | 3/1993 | Buell |
| 5,267,992 | A | | 12/1993 | Van Tillbug |
| 5,308,346 | A | | 5/1994 | Sneller et al. |
| 5,342,342 | A | | 8/1994 | Kitaoka |
| 5,360,419 | A | | 11/1994 | Chen |
| 5,386,595 | A | | 2/1995 | Kuen et al. |
| 5,494,554 | A | | 2/1996 | Edwards et al. |
| 5,509,914 | A | | 4/1996 | Osborn, III |
| 5,539,019 | A | * | 7/1996 | Suskind ................ A61F 13/534 428/407 |
| 5,558,659 | A | | 9/1996 | Sherrod et al. |
| 5,569,234 | A | | 10/1996 | Buell et al. |
| 5,634,916 | A | | 6/1997 | Lavon et al. |
| 5,649,916 | A | | 7/1997 | DiPalma et al. |
| 5,702,378 | A | | 12/1997 | Widlund et al. |
| 5,716,349 | A | | 2/1998 | Taylor et al. |
| 5,772,845 | A | | 6/1998 | Farrington, Jr. et al. |
| 6,110,158 | A | | 8/2000 | Kielpikowski |
| 6,240,569 | B1 | | 6/2001 | VanGompel et al. |
| 6,367,089 | B2 | | 4/2002 | VanGompel et al. |
| 6,663,611 | B2 | | 12/2003 | Blaney et al. |
| 6,921,393 | B2 | | 7/2005 | Tears et al. |
| 2003/0206979 | A1 | * | 11/2003 | Dvoracek ........... A61F 13/8405 424/766 |
| 2004/0210205 | A1 | | 10/2004 | Van Gompel et al. |
| 2015/0065974 | A1 | | 3/2015 | Michels |
| 2016/0089324 | A1 | * | 3/2016 | Nijakowski ............ A61K 8/345 514/355 |
| 2017/0189320 | A1 | * | 7/2017 | Chiou ...................... A61Q 1/02 |

FOREIGN PATENT DOCUMENTS

| | | | | | |
|---|---|---|---|---|---|
| CN | 105246515 | A | * | 1/2016 | ........... A61L 15/225 |
| EP | 1654013 | B1 | * | 11/2009 | .............. A61P 31/04 |
| RU | 92314 | U1 | | 3/2010 | |
| WO | 99/000093 | A1 | | 1/1999 | |
| WO | 2007/057211 | A1 | | 5/2007 | |

(Continued)

OTHER PUBLICATIONS

Pubmed: acrylic acid, 1 pages, 2025.*

International Searching Authority, International Search Report, PCT/US2018/054671, Dated Jan. 24, 2019.

International Searching Authority, Written Opinion of the International Searching Authority, PCT/US2018/054671, Dated Jan. 24, 2019.

*Primary Examiner* — Kyle A Purdy

(74) *Attorney, Agent, or Firm* — Reichel Stohry Dean LLP; Mark C. Reichel; Natalie J. Dean

(57) ABSTRACT

Disclosed are compositions, materials, garments, devices, and methods for controlling or neutralizing offensive odors associated with mammalian urine. For example, disclosed are personal care products (e.g., diapers), deodorizing colloidal compositions, urine-based fertilizers, portable urination systems, and methods of their use. Such deodorizing colloidal compositions, urine-based fertilizers, portable urination systems are characterized in that they contain an acrylate polymer comprising at least one acrylic acid monomer or salt thereof, which imparts an odor-neutralizing effect. Also provided are methods of recovering water from the systems disclosed herein.

19 Claims, 6 Drawing Sheets

(56) References Cited

FOREIGN PATENT DOCUMENTS

| | | | |
|---|---|---|---|
| WO | 2010/127442 | A1 | 11/2010 |
| WO | 2011/137393 | B1 | 11/2011 |
| WO | 2015/100440 | A1 | 7/2015 |

* cited by examiner

MATERIALS AND METHODS FOR DEODORIZATION OF MAMMALIAN URINE

PRIORITY AND RELATED APPLICATIONS

The present application is related to, claims the priority benefit of, and is a U.S. continuation patent application of, U.S. patent application Ser. No. 16/754,128, filed Apr. 6, 2020, which is related to, and is a U.S. National Stage Patent Application of, PCT Patent Application Serial No. PCT/US2018/054671, filed Oct. 5, 2018, which is related to, and claims the priority benefit of, U.S. Provisional Patent Application No. 62/568,920, filed Oct. 6, 2017. The contents of each of the aforementioned patent applications are incorporated herein directly and by reference in their entirety.

BACKGROUND

Absorbent products intended readily to absorb discharged body fluids are well known in the art. For example, disposable diapers, adult incontinence products, training pants, and feminine care products often employ water-swellable, generally water-insoluble, absorbent materials known in the art as superabsorbents. Such superabsorbents are generally capable of absorbing at least about 10, and up to 100, times their weight in water. The use of such superabsorbent materials in absorbent products greatly increases the absorbent capacity of the absorbent products while allowing for a reduction in their bulk. In recent years, the concentration of superabsorbent materials used in absorbent products has been increasing. As the concentration of superabsorbent materials used in disposable products increases, however, so do the malodors associated with such products, particularly due to the objectionable smells associated with ammonia and amines found in mammalian urine. The volatility of these substances makes them quite noticeable even when only small amounts of urine are present.

Various different odor control additives have been incorporated into such absorbent products. Unfortunately, however, such compositions have proven ineffective in obtaining the full level of odor control desired in many applications. As such, a need exists for an efficient and effective manner to reduce the malodors associated with absorbent without relying completely on masking agents such as perfumes.

BRIEF SUMMARY

This invention relates to the controlling or neutralizing of offensive odors of mammalian urine. In particular, the present invention relates to personal care products (e.g., diapers, pads), deodorizing colloidal compositions, urine-based fertilizers, portable urination systems, and methods of their use. Such deodorizing colloidal compositions, urine-based fertilizers, portable urination systems are all characterized in that they contain an acrylate polymer comprising at least one acrylic acid monomer or salt thereof, which imparts a odor-neutralizing effect.

Thus, one aspect of the invention provides a personal care product, comprising an absorbent core mixed with an odor-neutralizing polymer, and a solid support; wherein the absorbent core and the solid support are adjacently disposed; the absorbent core comprises a dry, solid, water-swellable polymeric sorbent; and the odor-neutralizing polymer comprises an acrylate polymer comprising at least one acrylic acid monomer or salt thereof.

Another aspect of the invention provides a colloidal composition, comprising an odor-neutralizing polymer and an aqueous solution, wherein the odor-neutralizing polymer is dispersed in the aqueous solution; and the odor-neutralizing polymer comprises an acrylate polymer comprises at least one acrylic acid monomer.

Yet another aspect of the invention provides a waterless urination system, comprising a disposable container; a toilet bowl; and a tube connecting the toilet bowl to the disposable container; wherein the tube is at least partially hollow; and the disposable container comprises a dry, solid, water-swellable polymeric sorbent comprising an odor-neutralizing polymeric compound comprising one or more acrylic acid monomers or salts thereof, and optionally one or more additives.

Still another aspect of the invention provides a fertilizer composition, comprising urine; and an odor-neutralizing polymeric sorbent comprising an acrylate polymer, and optionally one or more additives; wherein the acrylate polymer comprises at least one acrylic acid monomer.

Additionally, provided herein is a method for reducing urine odor in a personal care product to a level below human detection, comprising exposing a urine sample to a personal care product comprising an absorbent core mixed with one or more odor-neutralizing polymers, and a solid support; wherein the absorbent core and the solid support are adjacently disposed; the absorbent core comprises a dry, solid, water-swellable polymeric sorbent; and the odor-neutralizing polymer comprises an acrylate polymer comprising at least one acrylic acid monomer or salt thereof.

Another aspect of the invention provides method for reducing urine odor to a level below human detection, comprising exposing a urine sample to a composition comprising an odor-neutralizing polymer comprising an acrylate polymer, wherein the acrylate polymer comprises at least one acrylic acid monomer.

Yet another aspect of the invention provides a reducing urine odor to a level below human detection comprising exposing a urine sample a waterless urination system comprising a disposable container; a toilet bowl; a tube connecting the toilet bowl to the disposable container; and a movable object disposed at the center of the toilet bowl and covering the opening of the tube connecting the toilet bowl to the disposable container; wherein the disposable container contains one or more odor-neutralizing polymers comprising one or more acrylic acid monomers or salts thereof, and optionally one or more additives; and the movable object allows for the free passage of liquid between the toilet bowl and the disposable container when open, and seals the toilet bowl from the disposable container when closed.

In preferred embodiments of the invention, the acrylic acid monomer is a moiety having the structure:

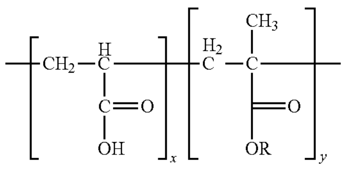

or salts thereof, wherein:

R is $C_{10}$-$C_{30}$-alkyl, $C_{10}$-$C_{30}$-haloalkyl, $C_{10}$-$C_{30}$-alkoxy, $C_{10}$-$C_{30}$-haloalkoxy, $C_{10}$-$C_{30}$-alkenyl, or polysiloxane;

x is an integer from 1 to about 10,000; and y is an integer from 0 to about 1,000.

BRIEF DESCRIPTION OF THE DRAWINGS

The present disclosure will be more fully understood, and further features will become apparent, when reference is made to the following detailed description and the accompanying drawings. The drawings are merely representative and are not intended to limit the scope of the claims.

DETAILED DESCRIPTION

Figure 1:
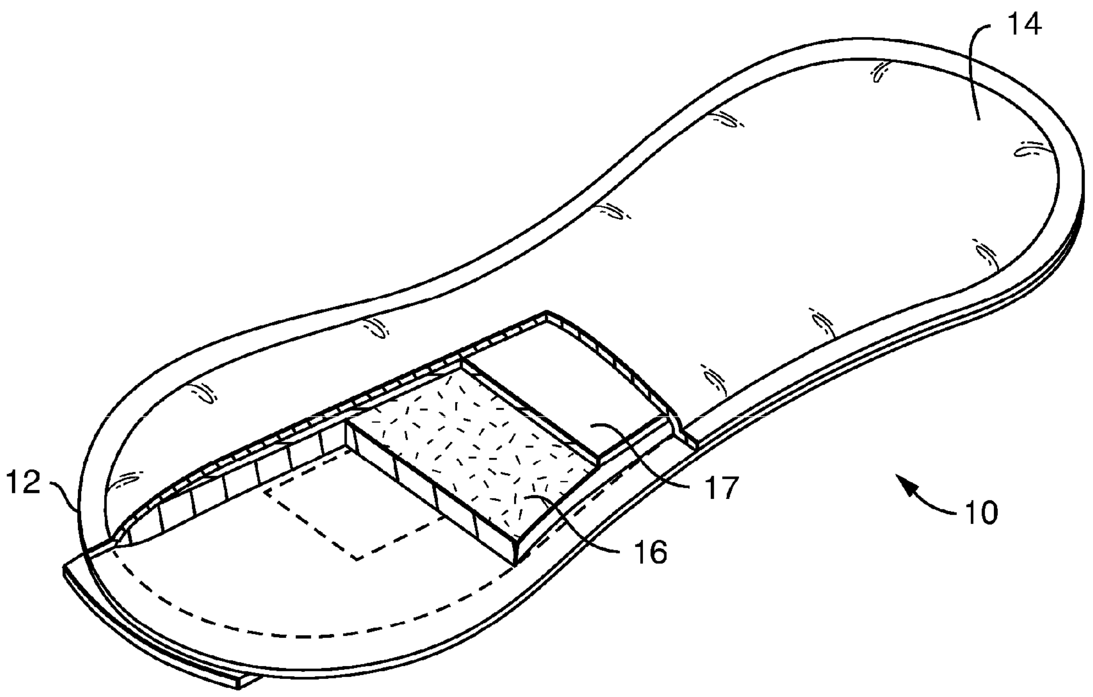
FIG. 1 is a drawing of a feminine hygiene product.

This invention relates to the controlling or neutralizing of offensive odors associated with mammalian urine.

Previous methods of controlling offensive odors, including those associated with animals, involved affecting the sense of smell. One older method was the use of a strong chemical such as formaldehyde which reacts with the olfactory epithelium (sense organ) so that it is physiologically inactivated, that is, the sense of smell is temporarily destroyed. Another method, currently popular, is to overwhelm the sense of smell with a very strong odor so that the objectionable odor is no longer detected. These strong odors are usually perfumes and are commonly called masking agents. These are very persistent odors and often have a sweet odor so that the masking agent itself can be objectionable.

The present invention thus relates to a deodorizing personal care products, such as diapers, training pants, absorbent underpants, adult incontinence products, feminine hygiene products, and the like, and methods of use thereof. Such personal care products can be made in one or several layers and are intended for absorption of urine. The present personal care products are characterized in that they contain, in an inner area or layer, an acrylate polymer comprising at least one acrylic acid monomer or salt thereof, which imparts an odor-neutralizing effect.

The present invention also relates to deodorized colloidal compositions, urine-based fertilizers, portable urination systems, and methods of their use. Such deodorizing colloidal compositions, urine-based fertilizers, portable urination systems are all characterized in that they contain an acrylate polymer comprising at least one acrylic acid monomer or salt thereof, which imparts a odor-neutralizing effect.

Definitions

"Alkyl" refers to a fully saturated cyclic or acyclic, branched or unbranched carbon chain moiety having the number of carbon atoms specified, or up to 30 carbon atoms if no specification is made. For example, alkyl of 10 to 30 carbon atoms includes decyl, undecyl, dodecyl, tridecyl, tetradecyl, pentadecyl, hexadecyl, heptadecyl, octadecyl, nonadecyl, eicosyl, heneicosyl, docosyl, tricosyl and tetracosyl. In certain embodiments, a straight chain or branched chain alkyl has between 10 and 30 carbon atoms in its backbone.

The terms "alkoxyl" or "alkoxy" as used herein refers to an alkyl group, as defined below, having an oxygen moiety attached thereto.

"Alkenyl" refers to any cyclic or acyclic, branched or unbranched unsaturated carbon chain moiety having the number of carbon atoms specified, or up to 30 carbon atoms if no limitation on the number of carbon atoms is specified; and having one or more double bonds in the moiety. Alkenyl of 10 to 30 carbon atoms is exemplified by decenyl, undecenyl, dodenyl, tridecenyl, tetradecenyl, pentadecenyl, hexadecenyl, heptadecenyl, octadecenyl, nonadecenyl, eicosenyl, heneicosoenyl, docosenyl, tricosenyl, and tetracosenyl, in their various isomeric forms, where the unsaturated bond(s) can be located any wherein the moiety and can have either the (Z) or the (E) configuration about the double bond(s).

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "halogen" designates —F, —Cl, —Br, or —I.

The term "haloalkyl" means at least one halogen, as defined herein, appended to the parent molecular moiety through an alkyl group, as defined herein.

The term "haloalkoxy" means at least one halogen, as defined herein, appended to the parent molecular moiety through an alkoxy group, as defined herein.

The term "polysiloxane" means a group represented by the formulae $-(OSiH_2)_nOH$ and $-(OSiH_2)_n$. Polysiloxanes include branched compounds, the defining feature of which is that each pair of silicon centres is separated by one oxygen atom.

As used herein, the definition of each expression, e.g., alkyl, m, n, etc., when it occurs more than once in any structure, is intended to be independent of its definition elsewhere in the same structure.

The term "mammal" includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals, including work animals as well as household pets, such as cattle, pigs, horses, sheep, goats, cats, and/or dogs; and/or birds, including commercially relevant birds such as chickens, ducks, geese, quail, and/or turkeys. Preferred mammals are humans, dogs, and cats.

For purposes of this invention, the chemical elements are identified in accordance with the Periodic Table of the Elements, CAS version, *Handbook of Chemistry and Physics,* 67th ed., 1986-87, inside cover.

Odor Neutralizing Polymers

Aspects of the compositions of the present invention comprise odor-neutralizing polymers and copolymers. An example of the polymers and copolymers of the compositions of the present invention comprise acrylic acid based polymers or copolymers (AAP). Acrylic acid polymer products are produced or distributed by several companies (Table 1).

TABLE 1

Leading Companies and AAP Products

| Trademarks | Company Name | Headquarters |
|---|---|---|
| Carbopol ®, Pemulen ®, Noveon ® | Noveon, Inc. | Brecksville, OH |
| Acritamer ® | RITA Corporation | Crystal Lake, IL |
| Acrisint ® | 3V-Sigma | Weehawken, NJ |
| Aqupec ® | Sumitomo Seika Chemicals Company, Ltd. | Osaka, Japan |
| Thixol ® 100C | Coatex | Caluire, France |
| Hypan ® | Kingston Hydrogels | Dayton, NJ |
| Acrysol ® ASE-75, Acumer ® 1510 | Rohm & Haas Company, Inc. | Philadelphia, PA |
| Sanwet ® | Hoechst Celanese Corp | Portsmouth, VA |
| Hoe S 3915 | Hoechst Aktiengesellschaft | Frankfurt am Main, Germany |

Many different types of AAPs are produced, and all AAPs that are capable of deodorizing mammalian urine are contemplated by the present invention. For example, AAPs can be linear polymers of acrylic acid, or polymers crosslinked with polyalkenyl ethers or divinyl glycol or other cross-linkers. It has been reported that when these AAPs have been polymerized under the same conditions and using the same recipe as the crosslinked grades, but without the crosslinked monomer, the weight average molecular weights are in the order of about 500,000 ("Molecular weight of Carbopol® and Pemulen® polymers", Noveon, Inc., 2001, TDS 222). The molecular weight of crosslinked polymers is in the billions. There are two major types of crosslinked polymers:

(1) homopolymers, which are polymers of acrylic acid crosslinked, for example with allyl sucrose or allylpentaerythritol; and (2) copolymers, which are polymers of acrylic acid modified by long chain ($C_{10}$-$C_{30}$) alkyl acrylates, and cross-linked, for example with allylpentaerythritol.

The general structures of two most frequently used acrylic homopolymers Carbopol® and copolymer Pemulen® are presented below.

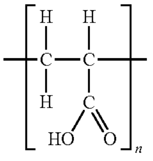

Carbopol®

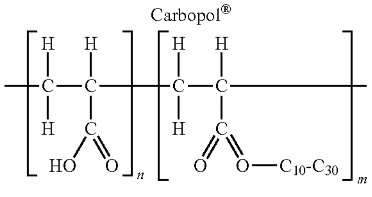

Pemulen®

In some embodiments, disclosed herein are odor-neutralizing polymers that comprise one or more acrylic acid monomers. In some such embodiments, the one or more acrylic acid monomer is a moiety having the structure:

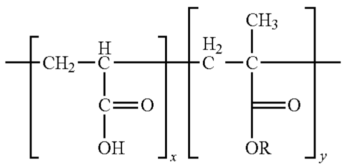

or salts thereof, wherein:

R is $C_{10}$-$C_{30}$-alkyl, $C_{10}$-$C_{30}$-haloalkyl, $C_{10}$-$C_{30}$-alkoxy, $C_{10}$-$C_{30}$-haloalkoxy, $C_{10}$-$C_{30}$-alkenyl, or polysiloxane;

x is an integer from 1 to about 10,000; and y is an integer from 0 to about 1,000.

In some embodiments, R is $C_{10}$-$C_{30}$-alkyl. In other embodiments, y is 0. In preferred embodiments, x is an integer from about 1000 to about 5000; and y is 0.

Although linear acrylic acid polymers are soluble in polar solvents, such as water, crosslinked polymers do not dissolve in water, instead they swell. In a solution of crosslinked polymers with a concentration of up to 1%, no significant swelling occurs until the crosslinked polymers are partially neutralized with an appropriate base to form a salt. When this salt dissolves and ionizes, the crosslinked polymers swell into a thickened form ("Application technology for Carbopol® resins and cosmetic formulations", Noveon, Inc., 2001, TDS 60).

The backbone of acrylic acid homopolymers is the same, and the main difference between these types of polymers is related to crosslink density and molecular weight, rather than that type of monomer that is used as the crosslinking agent. With very minor adjustments in the crosslinker density, one can produce a large number of AAP products similar in gross molecular structure but varying in application properties, for example, viscosity. Crosslink density can be varied by minor shifts in position of the crosslinker on the acrylic backbone.

The present invention comprises compositions of linear polymers or copolymers that deodorize mammalian urine. The terms polymers and copolymers are used interchangeably herein, and polymer includes copolymer. Thus, one embodiment of the present invention comprises compositions that deodorize mammalian urine.

The compositions of the present invention comprise acrylic acid polymers and copolymers. A composition comprises an effective amount of an acrylic acid polymer or copolymer in a pharmaceutically acceptable carrier or excipient composition. For example, a composition comprises an AAP in range of about 1 microgram to 5 g per dose or application, or a composition may comprise from about 0.001% wt to about 99% wt of one or more AAPs. Ranges of AAPs in compositions include from about less than 0.05%, from about 0.001% wt. to less than about 0.05% wt, from about less than 0.1% wt, from about 0.001% wt to about 25% wt, from about 0.001% wt to about 15% wt, from about 0.001% wt to about 50% wt, from about 0.001% wt to about 55% wt, from about 0.001% wt to about 75% wt, from about 0.001% wt to about 85% wt, from about 0.001% wt to about 90% wt, from about 0.001% wt to about 95% wt, or about less than 0.05% wt, about less than 0.10% wt, about less than 0.5% wt, about less than 1.0% wt, about less than 5.0% wt, about less than 10.0% wt, about less than 25.0% wt, about less than 50% wt, about less than 65% wt, about less than 75% wt, about less than 80% wt, about less than 90% wt, or about less than 95% wt.

The present invention comprises synthetic water soluble and water-swelling polymers. These polymers are commonly synthesized from water-soluble monomers, like: acrylic acid (AA) and its sodium salt, acrylamide (AM), hydroxy ethyl methacrylate (HEMA), hydroxy ethyl acrylate (HEA), vinylyyrolidone (VP), quaternary ammonium salt, like dimethyldiallyl ammonium chloride (DMDAAC) and etc. They generally follow the free radical polymerization mechanism. The synthesis is commercially implemented by various processes including aqueous solution polymerization, inverse suspension polymerization, and inverse emulsion polymerization.

Solution polymerization is commonly used in the synthesis of linear, low molecular weight water-soluble polymers. Poly(acrylic acid) and its copolymers, and polyacrylamide and its copolymer with DMDAAC are polymerized in solution. In order to synthesize the high molecular weight poly(acrylic acid), polyacrylamide and their copolymers, inverse suspension/emulsion processes are used. In the solution process, the water-soluble monomers are polymerized in a homogenous aqueous solution in the presence of free-radical initiators, mostly redox couples. The solution process requires low operating costs, principally in the avoidance of materials such as organic phases and emulsifiers. Linear, high molecule weight, polyacrylamide-based polymers are commercially synthesized through inverse emulsion (W/O, 0.05-1 μm) polymerization, while the production of lightly crosslinked, poly(acrylic acid)-based polymers is generally manufactured by inverse suspension (W/O, 0.05-2 mm) polymerization. In both cases, the aqueous monomer mixture (i.e., water phase) is emulsified/suspended in an aliphatic or aromatic hydrocarbon phase (i.e., oil phase), and the size of particles strongly depends on the chemical and physical properties of the emulsifiers or dispersing agents used.

Nonlimiting examples of such polymers or copolymers include, but are not limited to, linear acrylic acid-based polymers, crosslinked acrylic acid-based polymers, high molecular weight crosslinked acrylic acid-based polymers, polymers of acrylic acid crosslinked with allyl sucrose, polymers of acrylic acid crosslinked with allylpentaerythritol, polymers of acrylic acid, modified by long chain ($C_{10}$-$C_{30}$) acrylates, polymers of acrylic acid, modified by long chain ($C_{10}$-$C_{30}$) acrylates that are crosslinked with allylpentaerythritol, copolymers of acrylic acid, modified by long chain ($C_{10}$-$C_{30}$) alkyl acrylates, and copolymers of acrylic acid, modified by long chain ($C_{10}$-$C_{30}$) alkyl acrylates crosslinked with allylpentaerythritol, polymers of acrylic acid crosslinked with divinyl glycol, homopolymers of acrylic acid crosslinked with an allyl ether of penaethritol, an allyl ether of sucrose or an allyl ether of propylene, polyvinyl carboxy polymers, carbomers, copolymers of $C_{10}$-$C_{30}$-alkyl acrylates and one or more monomers of acrylic acid, methacrylic acid or one of their simple esters crosslinked with an allyl ether of sucrose or an allyl ether of pentaerythritol, graft copolymers with acrylic polymer backbone and dimethylpolysiloxane side chains, hydrophilic/hydrophobic block copolymers such as ammonium acylates and acrylonitrogen copolymers, acrylic and acrylonitrogen copolymers, acrylic acid polyquaternium copolymers, polyglycols, hydrophobically modified ethylene oxide urethanes, polymers and copolymers marketed under the tradename Acusol by Rohm and Haas.

Personal Care Products

Some personal care products, particularly disposable absorbent incontinence products, are designed to be removed and discarded after a single use. By single use it is meant that the disposable absorbent incontinence product will be disposed of after being used once instead of being laundered or cleaned for reuse, as is typical of regular cloth underwear. Examples of some commercially available disposable absorbent incontinence products include diapers, training pants, pads, pantyliners, fitted briefs, belted shields, guards for men, protective underwear, and adjustable underwear.

In one particular aspect of the disclosure, a personal care product includes components such as: a liquid-permeable layer (e.g., body-side liner, surge layer, etc.), a liquid-impermeable layer which might have moisture vapor permeability or breathability (e.g., outer cover, ventilation layer, baffle, etc.), an absorbent core, an elastic member, and so forth. Several examples of such absorbent articles are described in U.S. Pat. No. 5,197,959 to Buell; U.S. Pat. No. 5,085,654 to Buell; U.S. Pat. No. 5,634,916 to Lavon, et al.; U.S. Pat. No. 5,569,234 to Buell, et al.; U.S. Pat. No. 5,716,349 to Taylor, et al.; U.S. Pat. No. 4,950,264 to Osborn, III; U.S. Pat. No. 5,009,653 to Osborn, III; U.S. Pat. No. 5,509,914 to Osborn, III; U.S. Pat. No. 5,649,916 to DiPalma, et al.; U.S. Pat. No. 5,267,992 to Van Tillburg; U.S. Pat. No. 4,687,478 to Van Tillburg; U.S. Pat. No. 4,285,343 to McNair; U.S. Pat. No. 4,608,047 to Mattingly; U.S. Pat. No. 5,342,342 to Kitaoka; U.S. Pat. No. 5,190,563 to Herron, et al.; U.S. Pat. No. 5,702,378 to Widlund, et al.; U.S. Pat. No. 5,308,346 to Sneller, et al.; U.S. Pat. No. 6,110,158 to Kielpikowski; U.S. Pat. No. 6,663,611 to Blaney, et al.; and WO 99/00093 to Patterson, et al.; each of which is incorporated by reference.

Many of the disposable absorbent incontinence underwear are similar in appearance, size, and shape to regular cloth underwear except that they are formed from a variety of different materials including absorbent and elastic materials. The absorbent materials allow the disposable absorbent incontinence underwear to absorb and retain body waste while the elastic material permits the disposable absorbent incontinence underwear to conform snugly to the anatomy of the wearer's torso.

Figure 4:
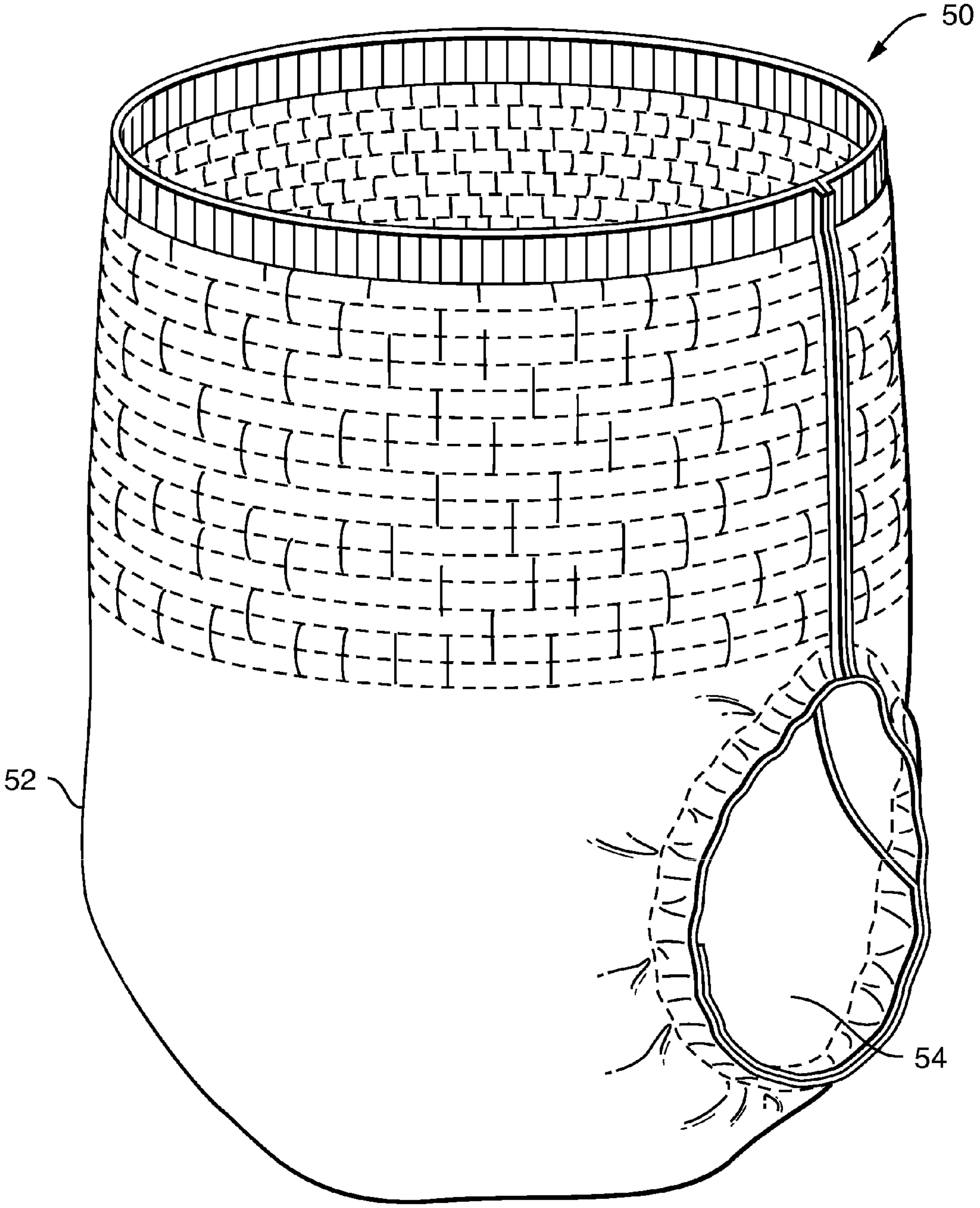
FIG. 4 is a drawing of an absorbent underpant.
Figure 5:
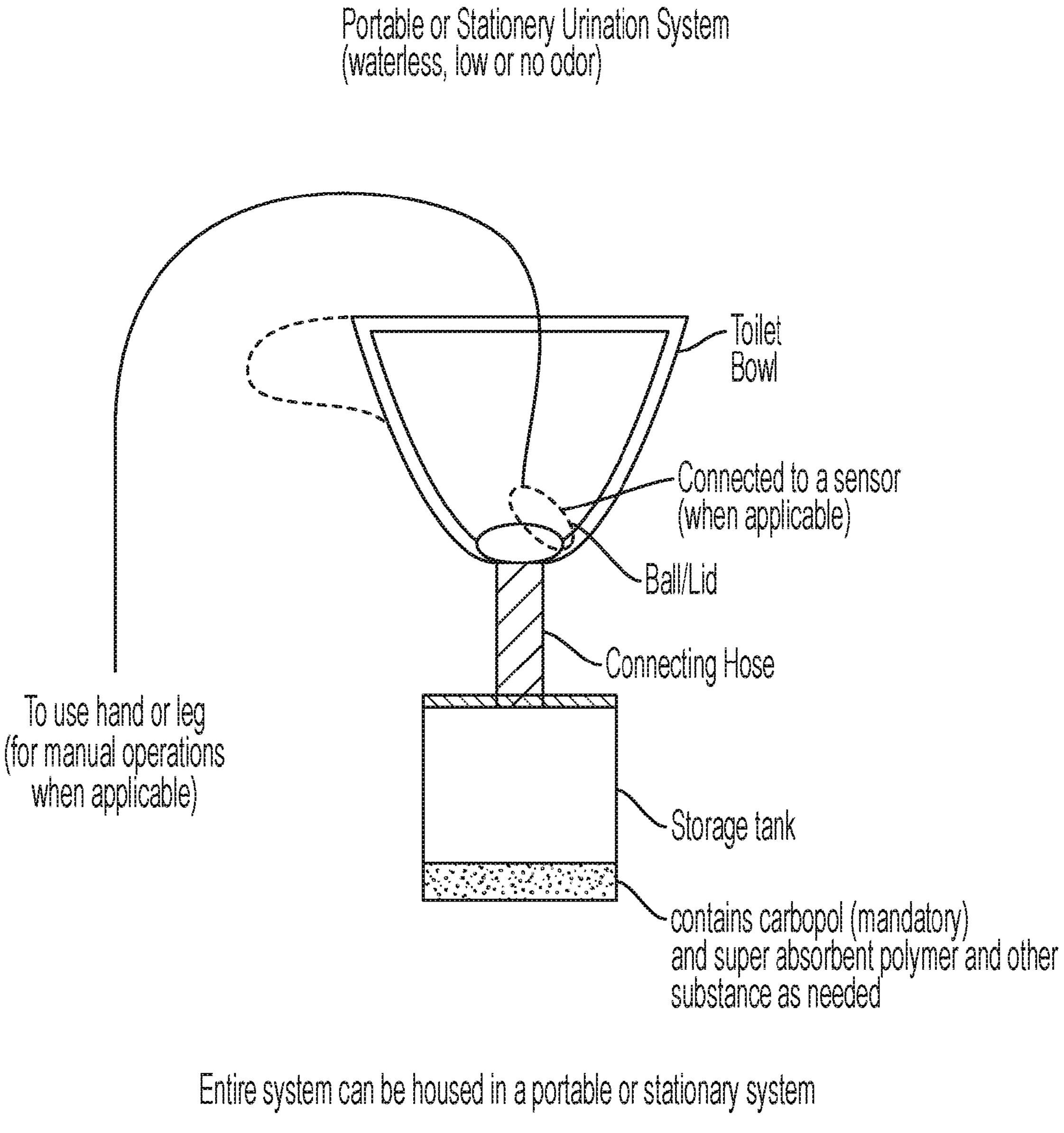
FIG. 5 is an exemplary embodiment of a waterless urination system of the invention.

Much of the disposable absorbent incontinence underwear sold today has a unitary configuration that is similar to regular cloth underwear in that the disposable absorbent incontinence underwear is constructed with a waist opening and a pair of leg openings and needs to be pulled onto the body like normal underwear. For example, absorbent underpant 50 as shown in FIG. 4 has an outer cover or baffle 52, a body-side liner 54, and an absorbent core (not shown). Further discussion regarding absorbent underpants can be found, for example, in U.S. Pat. No. 6,240,569 to Van Gompel; U.S. Pat. No. 6,367,089 to Van Gompel; and U.S. Patent Publication No. 2004/0210205 A1 to Van Gompel et al., which are incorporated herein by reference.

Other disposable absorbent incontinence underwear has an open configuration. By an open configuration it is meant that the disposable absorbent incontinence underwear does not have a waist opening and a pair of leg openings before it is positioned about the wearer's torso. Typically, disposable absorbent incontinence underwear having an open configuration has a relatively flat or convex shape before it is secured around the torso of the wearer. Commonly, disposable absorbent incontinence underwear having an open configuration has an approximately rectangular or hourglass shape. Such products are described in U.S. Pat. No. 4,500,316 to Damico, which is incorporated herein by reference.

A belted shield is still another type of a disposable absorbent incontinence product that has an open configuration and is held about the wearer's torso by a belt or a pair of straps, as described in U.S. Pat. No. 5,386,595 to Kuen et al. and U.S. Pat. No. 4,886,512 to Damico et al., which are incorporated herein by reference.

Another type of incontinence product is a guard for men, which resembles an absorbent pad that can conform to the male genitalia, as described in U.S. Pat. No. 5,558,659 to Sherrod et al., which is incorporated herein by reference.

While not ideal, some women wear feminine hygiene pads to absorb urine, such as the pad 10 shown in FIG. 1. Pad 10 includes a body-side liner 14, which extends to a pad perimeter 12. Underneath liner 14 is a tissue layer 17 and an absorbent core 16. The tissue may be substituted by a different odor-neutralizing polymer, such as a non-woven material.

Figure 2:
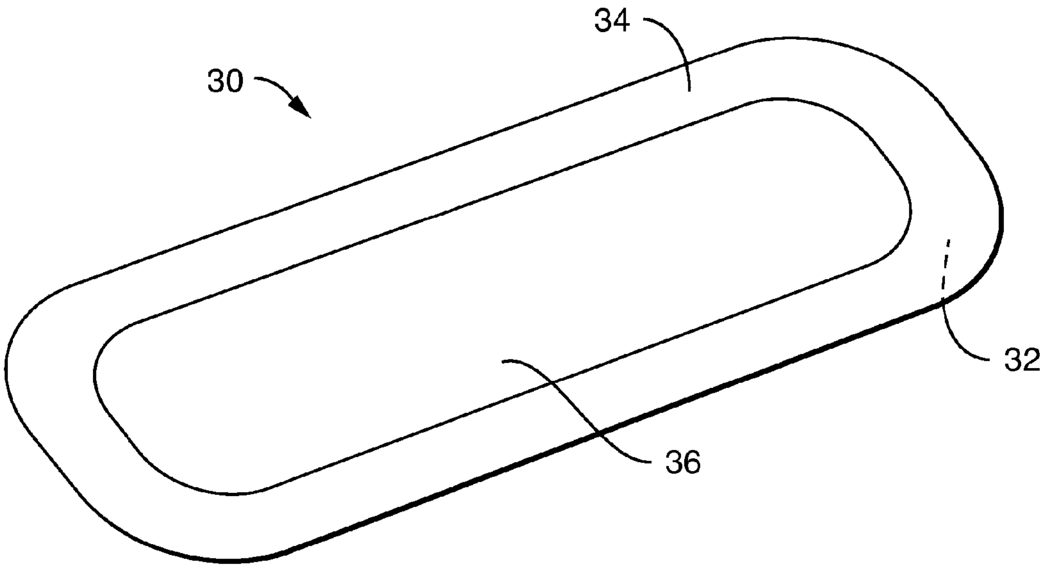
FIG. 2 is a drawing of an adult incontinence product.
Figure 3:
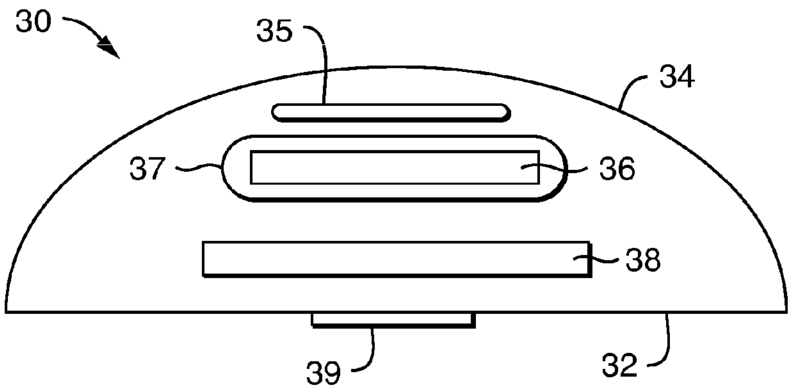
FIG. 3 is a drawing of a cross-section of an adult incontinence product.

Like feminine hygiene pads, feminine incontinence pads 30 as shown in FIGS. 2 and 3 have a baffle or outer cover 32, a body-side liner 34, and various layers in between, which includes an absorbent core 36. The absorbent core 36 has a body-facing surface adjacent the body-side liner 34, a garment-facing surface adjacent the outer-cover 32, and a pair of longitudinal sides. FIG. 3 is a cross-section of one non-limiting example of incontinence product. The body-side liner 34 is at the top of FIG. 3. The body-side liner 34 is designed to allow body fluid, particularly urine, to quickly pass through and be received by an absorbent core 36. The bodyside liner 34 is placed in contact with the genital area of a human body. A surge layer 35 may be positioned below the liner 34. The surge layer 35 acts as a reservoir to accept large surges of liquid and slowly release them to the subsequent layers. Below the surge layer 35 is the absorbent core 36 surrounded by a odor-neutralizing polymer in the form of a tissue wrap 37. The absorbent core 36 typically includes fluff and superabsorbent particles. The superabsorbent particles are loose and very small and therefore can escape onto the body or clothing unless contained. The odor-neutralizing polymer or tissue wrap 37 serves to prevent superabsorbent particles from migrating from the absorbent core to the user's skin. Under the odor-neutralizing polymer-wrapped absorbent core 36 is a baffle or outercover 32.

In one aspect of the invention, the odor-neutralizing polymer is disposed onto the absorbent core 36 by wrapping it at least around the body-facing surface and longitudinal sides. A solid support such as tissue wrap 37 may be fully wrapped about the absorbent core 36 so that the garment-facing surface is covered as well. In another aspect of the disclosure, the odor-neutralizing polymer covers as much as 100 percent the surface area of the body-facing surface of the absorbent core 36. In some such embodiments, the odor-neutralizing polymer is disposed onto the body-facing or the garment-facing surface of the absorbent core 36. In yet another aspect of the disclosure, two layers of odor-neutralizing polymer are used, one covering the body-facing surface of the absorbent core 36, and the other, the garment-facing surface of the absorbent core 36.

Many products also have an adhesive strip 39 to help hold the product in place during use by adhering it to the user's underclothes. Further, in one embodiment, there is an optional second absorbent layer, such as the airlaid layer 38 seen in FIG. 3. Airlaid layer 38 may be placed either below the tissue wrapped absorbent core 36 as shown, or above the tissue wrapped absorbent core 36.

Pads typically have a thickness of about 2.5 centimeters (cm) or less. Desirably, the thickness of a pad is less than about 1 cm. More desirably, the thickness of a pad is less than about 0.7 cm. A pad can have a length of from between about 15 cm to about 50 cm, and a width of from between about 2 cm to about 15 cm. Pads may have a rectangular, hourglass, or asymmetrical configuration.

A pantyliner, not shown, is a relatively thin absorbent pad having a thickness of about 1 cm or less. Desirably, the thickness of a pantyliner is less than about 0.5 cm. A pantyliner can have a length of from between about 15 cm to about 50 cm and a width of from between about 2 cm to about 15 cm. The pantyliner may have a rectangular, hourglass or asymmetrical configuration and may contain the same components as the pad shown in FIG. 3, or at least the body-side liner 34, the solid support such as tissue wrap 37, an absorbent core 36, and an outer cover 32.

In the present disclosure, the odor-neutralizing polymer is mixed into the absorbent core during the manufacture thereof. This ensures that the carbon particles are bound into the odor-neutralizing polymer and will not migrate to the article liner 34. In one embodiment of the disclosure, the solid support is in the form of tissue wrap 37 is made using a conventional cellulose tissue manufacturing process except that activated carbon particles or fibers are added to the pulp slurry in a concentration sufficient to result in a tissue having an effective amount of activated carbon. Conventional tissue products are made according to widely known papermaking-type processes. For example, U.S. Pat. No. 5,129,988 to Farrington, Jr.; U.S. Pat. No. 5,772,845 to Farrington, Jr. et al.; and U.S. Pat. No. 5,494,554 to Edwards et al. each discloses various tissue-making methods, which are incorporated by reference.

In some embodiments, the solid support is a super absorbent fiber, super absorbent laminate, or airlaid paper. In some embodiments, the super absorbent fiber has a fiber density of at least 1.4 g/mL. In some embodiments, the super absorbent fiber has a fiber density of about 1.4 g/mL. In some embodiments, the super absorbent fiber comprises a at least one synthetic fiber, at least one natural fiber, or a mixture thereof. In some embodiments, the at least one synthetic fiber comprises polyester.

More information concerning incontinence products can be found, for example, in U.S. Pat. No. 6,921,393 to Tears et al., which is incorporated by reference.

The present invention further provides methods for reducing urine odor in a personal care product to a level below human detection, comprising exposing a urine sample to a personal care product comprising an absorbent core mixed with one or more odor-neutralizing polymer, and a solid support; wherein the absorbent core and the solid support are adjacently disposed; the absorbent core comprises a dry, solid, water-swellable polymeric sorbent; and the odor-neutralizing polymer comprises an acrylate polymer comprising at least one acrylic acid monomer or salt thereof. In preferred embodiments, the urine sample is a human urine sample.

Colloidal Compositions

The current products for household urine control including odor distorters and eliminators use expensive chemicals and/or biological materials (e.g., enzymes, probiotics) that require special processes for manufacturing, processing, and/or handling and do not address the root cause of the smell. The present invention thus provides a type of product that offers a simple, less expensive solution by addressing the root cause of smell at its source. Besides the use of key odor-neutralizing polymers (e.g., AAPs, e.g., Carbopol®), these products are designed in such a way that other components (when needed) such as oils, fragrances, preservatives, surfactant, and the like, can be included in the product.

Thus, provided herein is colloidal composition, comprising an odor-neutralizing polymer comprising an acrylate polymer and an aqueous solution, wherein the odor-neutralizing polymer is dispersed in the aqueous solution; and the acrylate polymer comprises at least one acrylic acid monomer. In some embodiments, the colloidal composition of the invention further comprises one or more odor-neutralizing agents and/or odor-counteracting agents. For example, in some such embodiments, the colloidal composition of the invention comprises an oil, a fragrance, a preservative, or a surfactant. Exemplary odor-neutralizing agents include enzymes, peroxides, bicarbonate salts, surfactants or detergents, other polymers, lipids, oils, antibacterials, antimicrobials, probiotics, and the like. Exemplary odor-counteracting agent include preservatives, fragrances, chelating agents, probiotics, enzymes, and oxygen boosters. In some embodiments, the odor-neutralizing agent is a metal oxide. In some embodiments, the metal oxide is calcium oxide, zinc oxide, magnesium oxide, or titanium dioxide.

In some embodiments, the colloidal composition of the invention comprises a colorant or a taste-altering substance.

The colloidal compositions disclosed herein can be formulated by methods known in the art. For example, in some embodiments, the composition is formulated as a microemulsion, an emulsion, a suspension, a spray, a solution, a foam, a gel, or an emulsion gel.

The present invention further provides methods for reducing urine odor to a level below human detection, comprising exposing a urine sample to a composition (e.g., a colloidal composition) comprising an odor-neutralizing polymer comprising an acrylate polymer, wherein the acrylate polymer comprises at least one acrylic acid monomer. In some embodiments, the urine sample is a mammalian urine sample. In some such embodiments, the mammal is a non-human (e.g., a cat or a dog). In some such embodiments, the mammal is a felidae, equine, canine, bovine, primate, rodent, or bovidae.

Waterless Urination System

Waterless urination systems were introduced in 1990s. This kind of system is in high demand worldwide, especially where proper septic or sewer systems do not exist. In these regions, contaminated river, lake, and/or pond water can deliver pathogens in drinking water and thus lead to extremely unhealthy conditions for the inhabitants. Current waterless urination systems use oils, polymeric ball, or gel materials to deal with the ammonia and amines found in urine. These systems further comprise secondary features that are designed to channel urine to an existing sewer or septic line. Alternatively, these systems incorporate features designed to collect the urine in a tank for longer term storage, e.g., until the tank is transported to a treatment facility for disposal or for use in certain products such as fertilizers. The current waterless urination systems are stationary, expensive, and, in most cases, require an extended plumbing connection.

The waterless urination system of the present invention utilizes an in-situ neutralization of the basic components of urine (e.g., amines, amides, and the like) by an odor-neutralizing polymer (e.g., AAPs, e.g., Carbopol®).

Existing waterless technology may be optionally incorporated into the existing waterless system (e.g., polymer ball or oil(s)). However, the features of existing waterless technology related to channelizing the urine to a large storage tank or to a sewer or septic line or any other disposal line are not required by the present technology.

In some embodiments, disclosed herein is a waterless urination system, comprising a disposable container; a toilet bowl; and a tube connecting the toilet bowl to the disposable container comprising a dry, solid, water-swellable polymeric sorbent comprising a polymeric compound, comprising one or more odor-neutralizing polymers (e.g., polymers comprising at least one acrylic acid monomer or a salt thereof), and optionally one or more additives. In some such embodiments, the tube is at least partially hollow, and, preferably, is entirely hollow.

The present invention also contemplates a new type of toilet bowl, wherein urine odor is controlled by the opening and closing of a lid or ball at the center of the toilet bowl. The lid is open during urination and closed when not in use. This opening and closing mechanism can be executed by manual operation using a connector whose one end is connected to the ball or lid and the other end is connected to a device or paddle that is operated by the user. Alternatively, the opening and closing mechanisms is operated by a sensor (e.g., a UV ray).

Thus, in some embodiments, the waterless urination system further comprises a movable object disposed at the center of the toilet bowl and covering the opening of the tube connecting the toilet bowl to the disposable container. Such a movable object allows for the free passage of liquid between the toilet bowl and the disposable container when open, and seals the toilet bowl from the disposable container when closed.

In other embodiments, disclosed herein is a waterless urination system, comprising a disposable container; a bodyside interface; and a tube connecting the bodyside interface to the disposable container comprising a dry, solid, water-swellable polymeric sorbent comprising a polymeric compound, comprising one or more odor-neutralizing polymers (e.g., polymers comprising at least one acrylic acid monomer or a salt thereof), and optionally one or more additives. In some such embodiments, the tube is at least partially hollow, and, preferably, is entirely hollow.

Generally, the bodyside interface is an interface that facilities the transfer of urine and other waste products to the disposable container. Exemplary bodyside interfaces are polymer sheaths (e.g., a modified condom), cups, funnels, and catheters. In preferred embodiments, the polymer sheath comprises a biocompatible polymer (e.g., latex, nitrile, polyisoprene, or polyurethane). In some embodiments, the disposable container further comprises a connection unit. In some embodiments, the connection unit is connected to a second tube and the opposite end of the tube is connected to a waste storage unit, wherein the tube is at least partially hollow. In some embodiments, one end of disposable containers described herein can placed onto the subject's body and the other end on the floor or other location (e.g., of the spacecraft, flight or home floor). The collecting component of these devices can be designed and attached to the pipe/tube in such a way that they can be detached/replaced with a push of a button (easy insert/locking mechanism).

Urine and other disposed materials can be stored conveniently next or below the toilet or just outside the toilet room in the disposable container, which can act as a storage system. This storage system (without the toilet bowl) can be replaced with a new system (containing fresh odor-neutralizing polymer) when needed. In certain embodiments, the storage system has a ventilation attachment for release of any gaseous material that can accumulate over long term storage. The urine disposed materials can be used later for fertilizers, extracting important chemicals from urine, or other uses such as water recovery.

The waterless urination system disclosed herein eliminates the requirement of running water and channelizing urine safely to a sewer/septic/treatment system/center, which are of primary concern in areas where proper septic or sewer systems do not exist. The present invention thus provides a cost effective, portable or stationary waterless urination system.

The present invention further provides a method for reducing urine odor to a level below human detection comprising exposing a urine sample a waterless urination system comprising

- a disposable container; a toilet bowl;
- a tube connecting the toilet bowl to the disposable container; and
- a movable object disposed at the center of the toilet bowl and covering the opening of the tube connecting the toilet bowl to the disposable container;
- wherein the disposable container contains one or more odor-neutralizing polymers comprising one or more acrylic acid monomers or salts thereof, and optionally one or more additives; and
- the movable object allows for the free passage of liquid between the toilet bowl and the disposable container when open, and seals the toilet bowl from the disposable container when closed.

In preferred embodiments, the urine sample is a human urine sample.

In some embodiments, the waterless urination systems disclosed herein are suitable for use by terrestrial in-flights aircrew, space mission crew, bedridden individuals, wheelchair-bound individuals, long-distance drivers (e.g., freight drivers) and other individuals who have limitation in accessing a toilet and/or restricted movement.

Provided herein are methods of recovering water from the waterless urination system. In one aspect, the method comprises:

- contacting the contents of the disposable container disclosed herein with a salt thereby forming a mixture; and
- after a period of time, separating the water from the mixture.

In some embodiments, the salt is nontoxic. In some embodiments, the salt is selected from sodium chloride, magnesium chloride, calcium chloride, sodium bromide, magnesium bromide, calcium bromide, sodium iodide, magnesium iodide, calcium iodide, sodium sulfate, calcium sulfate, and magnesium sulfate.

In some embodiments, the water recovery method further comprises the step of contacting the contents of the disposable container with an acid, thereby adjusting the pH of the contents of the disposable container to at least less than 8.1. In some embodiments, the pH is adjusted to about pH 8, about pH 7.5, about pH 7, about pH 6.5, about pH 6, about pH 5.5, or about pH 5. In some embodiments, the acid is an inorganic acid. In some embodiments, the acid is hydrochloric acid, boric acid, phosphoric acid, or sulfuric acid.

In some embodiments, separating the water from the mixture comprises distillation or filtration.

Urea-Based Fertilizer

More than 90% of world industrial production of urea is destined for use as a nitrogen-release fertilizer. Urea has the highest nitrogen content of all solid nitrogenous fertilizers in common use. Therefore, it has the lowest transportation costs per unit of nitrogen nutrient. Many soil bacteria possess the enzyme urease, which catalyzes conversion of urea to ammonia ($NH_3$) or ammonium ion ($NH_4$) and bicarbonate ion ($HCO_3^-$). Thus urea fertilizers rapidly transform to the ammonium form in soils. Among the soil bacteria known to carry urease, some ammonia-oxidizing bacteria (AOB), such as species of *Nitrosomonas*, can also assimilate the carbon dioxide the reaction releases to make biomass via the Calvin cycle, and harvest energy by oxidizing ammonia (the other product of urease) to nitrite, a process termed nitrification. Nitrite-oxidizing bacteria, especially *Nitrobacter*, oxidize nitrite to nitrate, which is extremely mobile in soils because of its negative charge and is a major cause of water pollution from agriculture. Ammonium and nitrate are readily absorbed by plants, and are the dominant sources of nitrogen for plant growth. Urea is also used in many multi-component solid fertilizer formulations. Urea is highly soluble in water and is therefore also very suitable for use in fertilizer solutions (in combination with ammonium nitrate: UAN), e.g., in 'foliar feed' fertilizers. The most common impurity of synthetic urea is biuret, which impairs plant growth.

Provided herein is a urea-based fertilizer composition, comprising urine; and a polymeric sorbent comprising an acrylate polymer, and optionally one or more additives; wherein the acrylate polymer comprises at least one acrylic acid monomer. Exemplary additives include antibacterials, antimicrobials, and bioenzymatic materials.

In some embodiments, the fertilizer composition disclosed herein is provided as granules or prills. Preferably, the fertilizer composition disclosed herein is provided as granules. Urea absorbs moisture from the atmosphere and therefore is typically stored either in closed or sealed bags on pallets or, if stored in bulk, under cover with a tarpaulin. As with most solid fertilizers, storage in a cool, dry, well-ventilated area is recommended.

In certain aspects, the present invention provides methods of modulating plant growth comprising the steps of:

- obtaining a plant embedded in soil; and
- contacting the soil with the contents of the disposable container or the fertilizer of the present disclosure.

In certain embodiments, the method further comprises the step of contacting the soil with a liquid (e.g., water) after contacting the soil with the contents of the disposable container or the fertilizer of the present disclosure.

The invention now being generally described, it will be more readily understood by reference to the following examples, which are included merely for purposes of illustration of certain aspects and embodiments of the present invention, and are not intended to limit the invention.

EXEMPLIFICATION

Example 1

Figure 6:
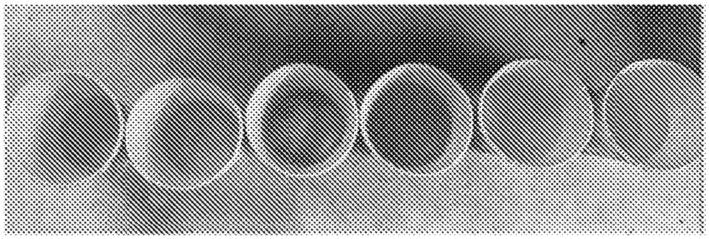
FIG. 6 depicts the samples described in Example 1.

| | |
|---|---|
| Materials | Human Urine, Water, Carbopol ® (Carbopol ® 981 NF), and a part of the absorbent core (consists of cellulose fluff pulps and superabsorbent polyacrylate granules) from a disposable diaper (Source: "Underwear for men" from RITEAID) that is labeled here as "DBM" |
| Method | Following samples were prepared in disposable cups and then covered with an aluminum foil. Samples were checked for visual appearance and odor daily for next 5 days. Samples 1 to 6 as described in FIG. 6, numbering starts from the left |

-continued

| | |
|---|---|
| | (i.e. Urine only sample is the left most). Samples: 1) Urine only, 2) Urine plus DSM, 3) Urine plus DBM, 4) Urine Plus DBM plus Carbopol ® 981, 4) Urine plus Carbopol 981, 5) Water plus DBM, 6) Water only (control). |
| Observations and conclusions: | Samples (fresh and aged samples) containing the Carbopol exhibited faint or no odor of urine. The bad odor from the samples# 1-2 (i.e. Urine with no Carbopol) intensified with the age of sample. This is due to the generation of ammonia over time. Whereas the samples, that are treated with Carbopol ®, showed no or minimal sign of ammonia. Carbopol ® undergoes in-situ neutralization by binding with the Ammonia/amide that is coming out from the urine. As a result, the reduction or complete elimination of odor of Urine is the samples that were treated with Carbopol. |

Example 2

Figure 7:
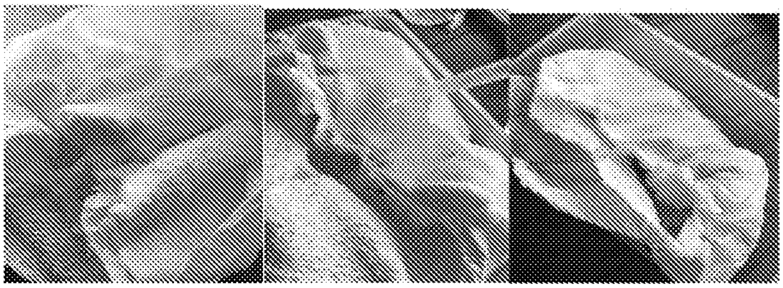
FIG. 7 depicts the samples described in Example 2.

| | |
|---|---|
| Materials | Human Urine, Water, Carbopol ® (Carbopol ® 981 NF), whole disposable diaper (Source: "Underwear for men" from RITEAID). |
| Method | One of the inner sides of the diaper was cut carefully to expose the inside base part of the diaper (i.e. cellulose fluff pulps with super absorbent). Then about half of a teaspoon of Carbopol ® powder was added evenly to the diaper base. Then about 50-100 ml of water or urine or both were added dropwise and evenly. Finally, the top cover was brought back to its original position and the side was tapped. Samples were stored at room temperature and were checked for visual appearance and odor daily for next 2-3 days. This is depicted in FIG. 7: Left: Diaper treated with Carbopol ® granules. Middle: Water addition onto the Diaper; Right: Diaper treated with Carbopol ® and Urine (Day 1). Samples are: 1) Untreated Diaper + Water, 2) Diaper treated with Carbopol ® + Water, 3) Diaper treated with Carbopol ® + Water + Urine, 4) Untreated Diaper (without Carbopol ®) + Urine. |
| Observations and conclusions: | Samples with Urine but treated with Carbopol ® exhibited almost no smell or faint smell of ammonia (bad odor) whereas the samples without Carbopol ® had fair amount of smell of ammonia which increases as the sample aged. Note: "Underwear for men" from Rite Aid Brand (that was used here) comes with "Omni-Odor Guard ™ Plus" but it did not address bad odor effectively as Carbopol ® does. |

Example 3

Urine with and without Carbopol® experiments were repeated confirming the above observations of Examples 1 and 2, and supports the in-situ neutralization of Carbopol® and hence the elimination of urine odor.

Superabsorbent polymer granules were removed from the diaper base, collected, and used for Examples 4 and 5.

Examples 4 and 5

Figure 8A:
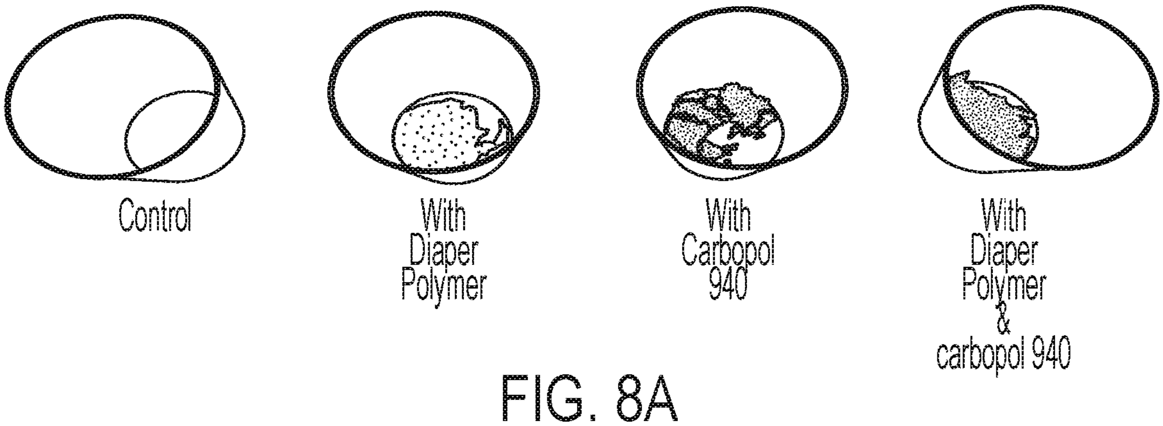
FIG. 8A depicts the samples described in Example 4.
Figure 8B:
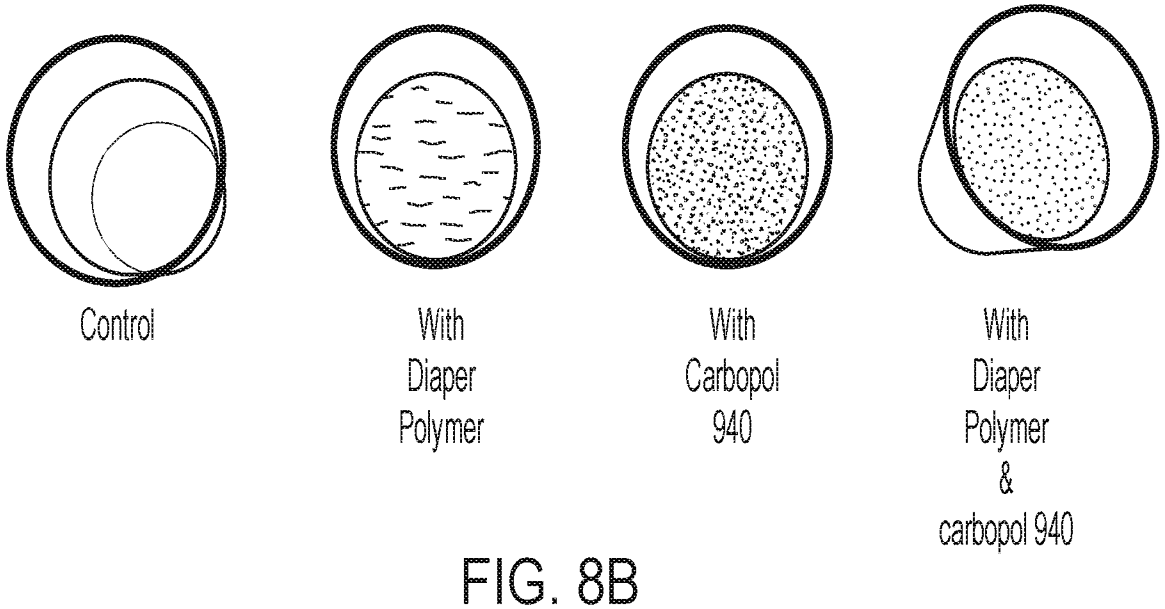
FIG. 8B depicts the samples described in Example 4.
Figure 9:
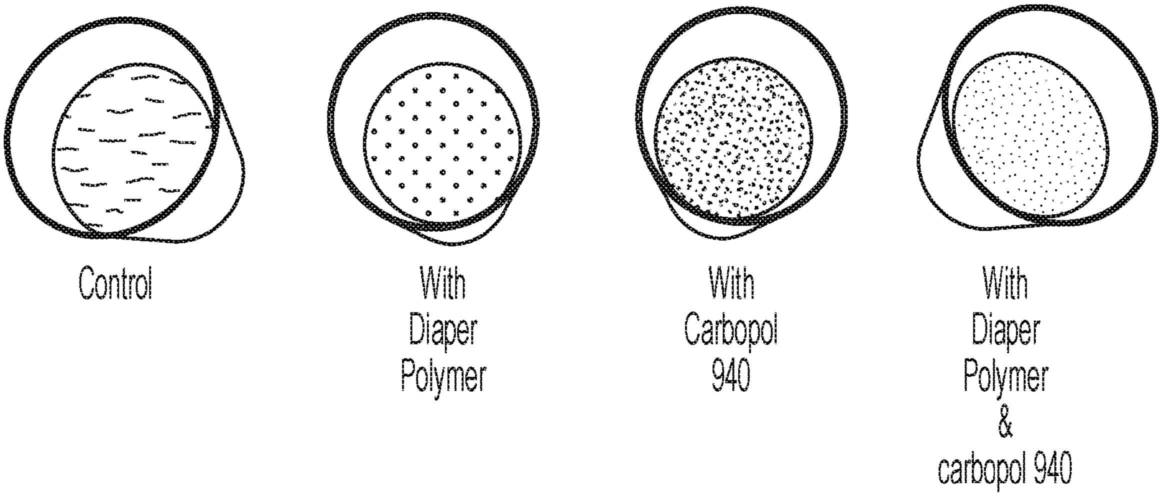
FIG. 9 depicts the samples described in Example 5.

| | |
|---|---|
| Materials | Human Urine, Water, Carbopol ® (Carbopol ® 940), Superabsorbent Polymer |
| Method | Example 4: Solid Powders (either Carbopol ® or Absorbent Polymer or both, ¼ of a teaspoon) were added to the empty plastic cups. Then Urine was added (5-10 mL) and stored with an aluminum foil cover. Samples were stored at room temperature and were checked for visual appearance and odor daily for next 2-3 days. This is depicted in FIG. 8A & B. Samples are: 1) Control (Urine only), 2) Urine and Super Absorbent (Diaper Polymer), 3) Urine, Carbopol ® (Carbopol ® 940), and Super Absorbent Example 5: The experiment was repeated (FIG. 9,) Legend (from left to right): 1) Control (Urine only), 2) Urine and Super Absorbent (Diaper Polymer), 3) Urine, Carbopol ® (Carbopol ® 940), and Super Absorbent |
| Observations and conclusions: | Odor of the samples follows the following trend: Sample 1 >>> Sample 2 >> Sample 2 > Sample 1 Sample 1 had almost no odor of Urine. The repeat experiment (Example 5) reproduced the results from Example 4. |

CONCLUSIONS

Examples 1-5 demonstrate an effective approach to address the bad odor of urine associated with diaper products, using odor-neutralizing polymers such as Carbopol®. Examples 1-5 demonstrate a process for eliminating bad odor of urine that is simple, cost-effective, safe, and easily incorporable into the exiting diaper designs without any structural changes or integrity of the diaper.

INCORPORATION BY REFERENCE

All US and PCT patent application publications and US patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The invention claimed is:

1. A personal care product, comprising:

a colloidal composition, comprising:

a) an odor-neutralizing polymer and an aqueous solution, wherein the odor-neutralizing polymer is dispersed in the aqueous solution; and the odor-neutralizing polymer comprises an acrylate polymer comprising at least one acrylic acid monomer having the structure

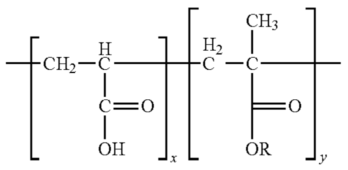

or salts thereof, wherein:

R is $C_{10}$-$C_{30}$-alkyl, $C_{10}$-$C_{30}$-haloalkyl, $C_{10}$-$C_{30}$-alkoxy, $C_{10}$-$C_{30}$-haloalkoxy, $C_{10}$-$C_{30}$-alkenyl, or polysiloxane;

x is an integer from 1 to about 10,000; and y is an integer from 0 to about 1,000;

b) an odor-neutralizing agent; and c) an odor-counteracting agent;

wherein said colloidal composition is incorporated into the personal care product selected from the group consisting of a diaper, a training pant, an absorbent underpant, an adult incontinence product, and a feminine hygiene product; and wherein the personal care product comprises a solid support and an absorbent core mixed with the colloidal composition, wherein the solid support and the absorbent core are adjacently disposed, and wherein the colloidal composition is mixed into the absorbent core during the manufacture of the absorbent core; and wherein the absorbent core has a body-facing surface adjacent to a body-side liner and a garment-facing surface adjacent an outer cover; and wherein the solid support comprises a tissue wrap made of cellulose tissue having a quantity of activated carbon therein.

2. The personal care product of claim 1, wherein the acrylate polymer is a polymeric compound comprising more than one acrylic acid monomer or salt thereof.

3. The personal care product of claim 1, wherein the acrylate polymer is linear or crosslinked.

4. The personal care product of claim 3, wherein the acrylate polymer is crosslinked.

5. The personal care product of claim 1, wherein the amount of the acrylate polymer in the polymeric sorbent is about 0.0001 wt % to about 95 wt %.

6. The personal care product of claim 1, wherein y is 0.

7. The personal care product of claim 1, wherein the acrylate polymer is an acrylate homopolymer.

8. The personal care product of claim 7, wherein the acrylate homopolymer is 2-propenoic acid homopolymer.

9. The personal care product of claim 1, wherein the acrylate polymer is an acrylate copolymer.

10. The personal care product of claim 9, wherein the acrylate copolymer comprises one or more acrylic acid monomers or salts thereof; and one or more $C_{10}$-$C_{30}$-alkylacrylate monomers or salts thereof.

11. The personal care product of claim 3, wherein the crosslinker is allyl sucrose, or a salt thereof; allyl pentaerythritol, or a salt thereof; allyl ether of propylene, or a salt thereof; or divinyl glycol, or salt thereof.

12. The personal care product of claim 1, wherein the odor-neutralizing agent is selected from an enzyme, a peroxide, a bicarbonate salt, a surfactant or detergent, another polymer, a lipid, an oil, an antibacterial, an antimicrobial, and a probiotic.

13. The personal care product of claim 12, wherein the odor-neutralizing agent is sodium bicarbonate.

14. The personal care product of claim 1, wherein the odor-neutralizing agent is a metal oxide.

15. The personal care product of claim 14, wherein the metal oxide is calcium oxide, zinc oxide, magnesium oxide, or titanium dioxide.

16. The personal care product of claim 1, wherein the odor-counteracting agent is selected from a preservative, a fragrance, a chelating agent, a probiotic, an enzyme, and an oxygen booster.

17. The personal care product of claim 1, further comprising a colorant or a taste-altering substance.

18. The personal care product of claim 1, wherein the absorbent core further comprises a pair of longitudinal sides.

19. The personal care product of claim 1, wherein the odor-counteracting agent comprises a probiotic.

* * * * *